United States Patent [19]
Seelig et al.

[11] Patent Number: 5,475,087
[45] Date of Patent: Dec. 12, 1995

[54] ANTAGONISTS OF HUMAN GRANULOCYTE-MACROPHAGE COLONY STIMULATING FACTOR DERIVED FROM THE CARBOXYL TERMINUS

[75] Inventors: Gail F. Seelig, Watchung; Julie E. Scheffler, Caldwell; Paul P. Trotta, Rutherford, all of N.J.

[73] Assignee: Schering Corporation, Kenilworth, N.J.

[21] Appl. No.: 192,310

[22] Filed: Feb. 4, 1994

Related U.S. Application Data

[63] Continuation of Ser. No. 778,911, filed as PCT/US90/03811, Jul. 12, 1990, which is a continuation-in-part of Ser. No. 379,846, Aug. 14, 1989, abandoned.

[51] Int. Cl.[6] .................................................. A61K 38/10
[52] U.S. Cl. ........................................ 530/326; 530/399
[58] Field of Search .................................... 530/326–330; 514/13–17

[56] References Cited

PUBLICATIONS

Weygand *Chem Ber* 103, 2437 (1970).
Moravek, *Coll Czech Chem Comm* 40, 1103 (1975).
Anfinsen, Principles that Govern the Folding of Protein Chains, Science 181:223 (1973).
Cantrell et al., Cloning, Sequence and Expression of a Human GM–CSF, Proc. Natl. Acad. Sci. USA 82:6250 (1985).
Gough et al., Molecular Cloning of cDNA Encoding a Murine Haematopoietic Growth Regulator, GM–CSF, Nature 309:763 (1984).
Grantham, Amino Acid Difference Formula to Help Explain Protein Evolution, Science 185:862 (1974).
Gualtieri et al.; GM–CSF Is An Endogenous Regulator of Cell Proliferation in Juvenile Chronic Myelogenous Leukemia, Clin. Res. 36:24A (1988).
Sege et al., Use of Anti–idiotypic Antibodies As Cell–surface Receptor Probes, Proc. Natl. Acad. Sci. USA 75:2443 (1978).
Kaushansky *Proc Natl Acad Sci* 83, 3101–5, 1986.

*Primary Examiner*—Jill Warden
*Assistant Examiner*—David Lukton
*Attorney, Agent, or Firm*—Paul G. Lunn; Norman C. Dulak; James R. Nelson

[57] ABSTRACT

Antagonists of GM-CSF are disclosed that comprise antibodies and anti-idiotypic antibodies specific for the carboxyl terminus of GM-CSF. These antagonists are useful for treating various diseases, the symptoms of which are increased by GM-CSF, and for lessening the effects of chemotherapy.

2 Claims, 6 Drawing Sheets

ANTAGONISTS OF HUMAN GRANULOCYTE-MACROPHAGE COLONY STIMULATING FACTOR DERIVED FROM THE CARBOXYL TERMINUS

The present application is a continuation of U.S. patent application Ser. No. 07/778,911 filed Jan. 9, 1992, which is the United States National application corresponding to International Application No. PCT/US90/03811, filed Jul. 12, 1990 now abandoned and designating the United States, which PCT application is in turn a continuation-in-part of U.S. Ser. No. 07/379,846, filed Aug. 14, 1989 now abandoned, the benefit of which applications is claimed pursuant to the provisions of 35 U.S.C. §§120,363 and 365 (C).

BACKGROUND OF THE INVENTION

Granulocyte-Macrophage Colony-Stimulating Factor (GM-CSF) is a polypeptide found in many mammals. GM-CSF is a lymphokine that stimulates the proliferation of a variety of undifferentiated progenitor cells involved in the immunological response. Various cellular components of the bone marrow are known to be stimulated by GM-CSF. See, MacDonald et al., J. Bone Mineral Res., 1 (2):227 (1986); Begley et al., Exp. Hematol., 13:956 (1985). Complementary DNAs (cDNAs) for GM-CSF have recently been cloned and sequenced by a number of laboratories, e.g., Gough et al., Nature 309:763 (1984), PCT Application No. 85/04188 (mouse); Cantrell et al., Proc. Natl., Acad. Sci 82:6250 (1985); European Patent Application No. 183,350 (human). Moreover, non-recombinant GM-CSF has been purified from various culture supernatants, e.g., U.S. Pat. No. 4,438,032 (Mo cell line); Burgess et al., Exp. Hematol. 9:893 (1981) (mouse); Sparrow et al., Proc. Natl. Acad. Sci., 82:292 (1985) (purification and partial amino acid sequence for mouse); Wu et al., Exp. Hematol., 12:267 (1984) (rat); Gasson et al., Science 230:1171 (1985) (human); Burgess et al., Blood, 69:43 (1987) (human). Among the human GM-CSFs, nucleotide sequence and amino acid sequence (primary structure) heterogeneity have been observed. For example, at the amino acid level of human GM-CSF, both threonine and isoleucine have been observed at position 100 with respect to the N-terminal alanine, suggesting that allelic forms, or polymorphs, of GM-CSF may exist within human populations.

Also, various leader sequences occur at the N-terminal portion of the amino acid sequence. These leaders may be of various lengths and amino acid composition, which may or may not affect biological activity. Often the leader sequence has a methionine residue at its N-terminal end. The native mature protein for GM-CSF is about 127 amino acid residues long. See PCT Application No. 86/03225 and PCT Application No. 86/00639 for comparisons of human GM-CSF sequence to the mouse and gibbon sequences, respectively.

Details about the secondary and tertiary structure for GM-CSF have yet to be elucidated, although a hydrophilicity plot for human GM-CSF has been constructed by Hopp and Woods [Proc. Natl. Acad. Sci. USA, 78:3824–8(1981)]. Many details about the mechanism of GM-CSF-induced cell proliferation remain a mystery.

Nevertheless, GM-CSF has been implicated as a factor in a number of disease states. The presence of elevated levels of GM-CSF concomitant with various disease states suggests that GM-CSF may have a role in autocrine or paracrine control of the growth of aberrant cells. Such control has been observed and/or postulated for leukemia/lymphomas, solid tumors, metastatic lesions, diseases involving macrophage infiltration, and cyclic neutropenia. It has been observed that the transformation of non-leukemogenic hematopoietic cell lines to the malignant phenotype was associated with the capacity to synthesize colony-stimulating factors (Hapel, et al. 1981; Schrader and Crapper, 1983). The hypothesis that autocrine stimulation by GM-CSF can result in leukemogenicity has been directly tested by using a retroviral vector to express GM-CSF in FDC-$P_1$, a factor-dependent murine cell line (Lang, R. A., Metcalf, D., Gough, N. M. et al., 1985), (see below). In these cases the colony-stimulating factor was IL-3 (multi-CSF). Thus, their results do suggest that appropriate antagonists for the CSF's could be employed as anti-leukemogenic agents.

The observation of constitutive expression of GM-CSF in patients with acute myelogenous leukemia (AML) [Young et al., J. Clin. Invest., 79:100–106 (1987)] has lead several investigators to urge caution [Begley et al., Leukemia, 1:1–8 (1987)] in the therapeutic application of GM-CSF in the treatment of AML and perhaps other diseased states.

Autostimulatory and autocrine synthesis have been implicated in the mechanism of oncogenesis of myeloid cells. Autologous production of particular cytokines resulting in autostimulation is believed to be a critical oncogenic step (Schrader et al., J. Cell Biochem. Abstract, 1988). Schrader et al. do suggest, however, that the "aberrant activation of lymphokine genes may be a common mechanism of oncogenic progression" given the appropriate target cell. It is consistent with this proposal that in a study of 24 cases involving myeloid leukemic cells, Mannoni et al., J. Cell Biochem. Abstract, (1988) report that these cells respond to GM-CSF by proliferating but not by differentiating.

Experimental induction of autocrine synthesis of GM-CSF [Gonda et al., Cell 51:675–686 (1987)] suggest that autocrine growth may be an important step in the progression to fully developed leukemia.

Studies demonstrating a direct relationship between autocrine stimulation by GM-CSF and leukemogenicity were based on the use of a retroviral vector to express GM-CSF in FDC-$P_1$, a factor-dependent murine cell line (Lang, R. A., Metcalf, D., Gough, N. M. et al., Cell 43:531–542, 1985). Virally infected cells were shown to synthesize GM-CSF and to proliferate in the absence of exogenous GM-CSF. This result contrasts with data obtained for the uninfected cells, which require exogenous IL-3 or exogenous GM-CSF for survival and proliferation. In addition, it was observed that the infected cell lines caused large, diffusely infiltrating tumor masses in syngeneic DBA mice. In distinction, no animals injected with FD cells developed transplanted leukemias during an observation period of 26 weeks. Thus, simply changing the ability of FD cells to synthesize GM-CSF appears to be sufficient to convert them to a tumorigenic phenotype.

Studies have been carried out by Laker et al., Proc. Natl. Acad. Sci. USA, 84:8458–8462 (1987) in which transfer of the GM-CSF gene into factor-independent cell lines resulted in the acquisition of factor-independent growth with an intermediate requirement for external stimulation followed by a second mutation which eliminated the need for external GM-CSF. The rate of transition of growth independence was highly correlated with the levels of GM-CSF produced, but could not be shown to be dependent upon a threshold level of GM-CSF. These studies suggest that the two steps of autocrine synthesis and autonomous growth were distinct but were interconnected in the progression toward a malignant state.

Antisera to GM-CSF significantly inhibit "spontaneous" growth associated with juvenile chronic myelogenous leukemia [Gualtieri et al., Clin. Res. 36(1):24A (1988)]. Santoli et al., J. Immunol. 139: 3348–3354 (1987) and Valtiei et al., J. Immunol. 138: 4042 (1987)] have established a T-lymphocytic leukemia derived cell line Tall 101. GM-CSF was shown to support the long-term growth of this cell line and to act synergistically with IL-3 to stimulate proliferation of T-lymphoblastic leukemia.

Constitutive expression of GM-CSF has been detected in several solid tumors. Evidence for the involvement of GM-CSF in tumor development is as follows.

Expression of GM-CSF in a lung squamous cell carcinoma was observed by Mano et al., Japan. J. Cancer Res., 78:1041–1043 (1987).

Binding of GM-CSF to a single class of high affinity receptors on small cell carcinoma cell lines has been reported by Baldwin et al., J. Cell Biochem. Abstracts (Suppl. 12A):97, (1988). In this same study these cell lines were shown to respond to GM-CSF in an in vitro colony growth assay.

Constitutive expression of GM-CSF was observed by Mano et al., Japan J. Cancer Res. 78:1041–1043 (1987) in a cell line established from lung large cell carcinoma derived from a patient. Constitutive expression of GM-CSF was observed by Mano et al., Japan J. Cancer Res. 78:1041–1043, (1987) in a cell line derived from a 43 year old male patient with a white blood cell count of 9000–10000/mm$^3$.

Dedhar and Gallaway, Abstracts of the Seventy-Ninth Annual Meeting of the American Association for Cancer Research, p. 51 (1988) and Dedhar et al., J. Cell Biochem. Abstracts (Supply. 12A):128 (1988) have reported that GM-CSF promotes proliferation of human osteogenic sarcoma cell lines MG-63 and HOS.

In studies by Hayashi et al., J. Cancer Res. 78: 1224–1228 (1987), a human bladder carcinoma cell line (HTB9) was found to express mRNA of the GM-CSF gene.

Ensoli et al., Congress on Cytokine Res. (1988) have reported that Kaposi's sarcoma (KS) cell lines derived from AIDS-KS patients express "abundant" levels of mRNA for GM-CSF. In describing a potential mechanism for autocrine growth stimulatory role in the initiation of KS-lesions, Biberfeld et al., J. Cell Biochem. Abstracts, p. 143 (1988) have noted the significant levels of several growth factors including that of GM-CSF.

Available data suggest that the metastatic process, particularly at late stages, may be enhanced by GM-CSF production. For example, an enhancement of lung metastases has been observed in mice which had a marked granulocytosis [Ishikawa and Ziff, Arthritis and Rheumatism 19: 1–3 (1976)]. Similarly, Glaves, Invasion Metastasis 3: 160 (1983), has reported data indicating that PMNs cause an accelerated pulmonary clearance of arrested melanoma cells, In vitro production of GM-CSF by a metastasizing cell line (TS/A) derived from a spontaneous mouse mammary carcinomas has been described [Nicoletti et al., Bio. J. Cancer, 52:215 (1985)], and a relationship was established in these studies between in vitro production of colony-stimulating factor and the capacity for spontaneous metastases. In a further recent series of experiments Nicoletti et al., Anti-cancer Res. 7: 695–700 (1987) investigated colony-stimulating factor production in various TS/A cell variants isolated by serial in vivo selection of lung metastatic nodules.

Studies in which transgenic mice carrying the murine GM-CSF gene expressed from a retroviral promoter resulted in elevated levels of GM-CSF in serum, urine, peritoneal cavity, and eye [Lang et al., Cell, 51:675–686 (1987)]. The mice developed lesions containing macrophages in striated muscle, and accumulations of macrophages in the eyes and in the peritoneal and pleural cavities. A high death rate was attributed to muscle wasting due to macrophage activation.

The following is a list of diseases related to macrophage infiltration in which a GM-CSF antagonist may be useful.

Firestein and Zvailfler, Arthritis and Rheumatism, 30, 857–863 (1987) have sought the factor responsible for monocyte activation in the phenotypes of peripheral blood monocytes and synovial fluid monocytes of patients with chronic inflammatory arthritis. The observation that there were only low levels of gamma interferon in synovial fluid and synovial tissue suggests that gamma interferon was likely not responsible for this activation [Firestein and Zvaifler, Arthritis and Rheumatism, 30, 864–871 (1987)].

The increase in the number of macrophages in the skin is important in cutaneous disorders. Diseases which fall into this category include infectious diseases such as Leishmaniasis and leprosy, and non-infectious diseases such as sarcoidosis and granuloma and annulare. Studies undertaken by Chodakewitz et al., J. Immunol. 140:832–836 (1988), have shown constitutive expression of GM-CSF by keratinocytes, which may play a role in the regulation of cutaneous macrophage responses. Danner et al., J. Invest. Derm., 89:339–340 (1987), have postulated, based on studies of neutrophil activation and oxygen radical release, that GM-CSF may play a role in the inflammatory skin diseases in which neutrophil activator is a "prominent feature".

Consistent with this possible role is the observation by Griel et al., Abstract of XIXth Meeting of the Society of Immunology, (1988), that the systemic treatment by GM-CSF of mice infected with Leishmania major enhances the parasitic burden rather than eliminating it. Thus, diseases associated with accumulations of macrophage aggregates and mononuclear phagocytes, such as sarcoidosis and the other diseases mentioned above, may be good targets for treatment with antagonists of GM-CSF.

Listeria monocytogenes [Cheers et al., Infection and Immunity, 56: 247–251 (1988)] infection was similarly associated with increased serum levels of GM-CSF.

Studies have suggested [Wright et al., Clinical Res. 36: 436A (1988)] that oscillations of neutrophil and monocyte production in the marrow which result in profound neutropenia at regular intervals are due to abnormal responses to GM-CSF by the myeloid progenitors. Several reports have noted marked but transient neutropenia in patients being treated with GM-CSF [Devereux et al., Lancet 121: 1523–1524 (1987)].

SUMMARY OF THE INVENTION

The present invention provides polypeptides, the amino acid sequences of which correspond to the sequence of residues at the carboxyl terminus of mature (native) human GM-CSF. More particularly, the polypeptides of the invention contain from about 5 to about 23 amino acid residues and have all or part of the amino acid sequence:

FORMULA I (SEQUENCE 1)

H—X(Ser)—X(Phe)—X(Lys)—X(Glu)—X(Asn)—
X(Leu)—X(Lys)—X(Asp)—X(Phe)—X(Leu)—
X(Leu)—X(Val)—X(Ile)—X(Pro)—X(Phe)—
X(Asp)—Cys—Trp—X(Glu)—X(Pro)—
X(Val)—X(Gln)—X(Glu)—OH, wherein the term X(Xaa) represents the group of synonymous amino acids to the amino acid Xaa.

Synonymous amino acids within a group have sufficiently similar physicochemical properties that substitution between members of the group will preserve the biological and immunological function of the polypeptide, Grantham, Science, 185:862–864(1974); and Dayoff et al., pages 89–99 in *Atlas of Protein Sequence and Structures,* Vol. 5 (National Biomedical Research Foundation, Washington, D.C., 1972). Preferably, the substitutions are selected from Table I and more preferably they are selected from Table II.

TABLE I

Preferred Groups of Synonymous Amino Acids.

| AMINO ACID | SYNONYMOUS GROUP |
|---|---|
| Ser | Ser, Ala, Thr, Gly, Asn |
| Phe | Phe, Tyr |
| Lys | Lys, Arg, Asn |
| Glu | Glu, Gln, Asp |
| Asn | Asn, Asp, Ser, Lys |
| Leu | Leu, Val |
| Asp | Asp, Asn, Glu |
| Val | Val, Ile, Ala, Leu |
| Ile | Ile, Val, Leu |
| Pro | Ala, Pro |
| Gln | Gln, Glu, His |

TABLE II

More Preferred Groups of Amino Acids.

| AMINO ACID GROUP | SYNONYMOUS |
|---|---|
| Ser | Ser, Ala, Thr |
| Phe | Phe |
| Lys | Lys |
| Glu | Glu, Asp |
| Asn | Asn, Asp |
| Leu | Leu |
| Asp | Asp, Glu, Asn |
| Val | Val, Ile |
| Ile | Ile, Val |
| Pro | Pro |
| Gln | Gln |

It will be appreciated that Tables I and II are merely points along a continuum of preferred amino acids that may be suitable for substitution It is clear that insertions and deletions of amino acids may also be made in the above defined sequence without altering biological and immunological functions, particularly if the insertions or deletions only involve a few amino acids, e.g., fewer than 2 or 3, and do not remove or displace amino acids which are critical to a functional conformation, Anfinsen, Science, 181: 223–230 (1973). Peptides differing from those of Formula I by such minor deletions or insertions come within the purview of the present invention.

Amino acid nomenclature recommended by the following reference is used throughout: Cohn, *Methods in Enzymology,* Vol. 106, pgs. 3–17 (Academic Press, New York, 1984); and IUPAC-IUB Commission, J. Bio. Chem., 247: 977–983 (1972).

Preferably the synonymous amino acid groups are those defined by Table I. More preferably, the synonymous amino acid groups are those defined in Table II; and most preferably the peptide of the invention is defined by the following sequence of amino acids:

FORMULA II (SEQUENCE 2)

H—Ser—Phe—Lys—Glu—Asn—
Leu—Lys—Asp—Phe—Leu—
Leu—Val—Ile—Pro—Phe—
Asp—Cys—Trp—Glu—Pro—
Val—Gln—Glu.

A preferred polypeptide contains the carboxyl terminal 18 amino acids of Formula I and the most preferred polypeptide contains the carboxyl terminal 18 amino acids of Formula II (corresponding to residues 110 through 127 of native human GM-CSF). The 18 amino acids represent the carboxyl terminus of native GM-CSF and the most hydrophilic (Residues 112 through 124) and hydrophobic (residues 125 through 127) regions and has the following sequence.

SEQUENCE 3

H—Leu—Lys—Asp—Phe—Leu—
Leu—Val—Ile—Pro—Phe—
Asp—Cys—Trp—Glu—Pro—
Val—Gln—Glu—

The invention includes peptides of Formula I with amino acid substitutions (between an amino acid of Formula II and a synonymous amino acid) at a single position or at multiple positions. The term "N-fold substituted" in reference to the peptides of Formula I is used to describe a subset of peptides wherein the amino acids of Formula II have been substituted by synonymous amino acids at no more than N positions. Thus, for example, the group of 1-fold substituted peptides of Formula I consists of 60 polypeptides for the preferred groups of synonymous amino acids, and 34 polypeptides for the more preferred groups of amino acids. The "1" in the term "1-fold substituted" means that the peptides of the groups differ from the most preferred sequence (Formula II) by no more than 1 amino acid substitution. Likewise, an "N-fold substituted" polypeptide refers to the group of polypeptides that differ from the most preferred sequence by no more than 4 amino acid substitutions.

Surprisingly, the polypeptides of the invention can be used as antigens to elicit the production of antibodies which can antagonize the biological effects of GM-CSF.

The invention also provides antibodies which specifically bind to GM-CSF and to the polypeptides of the invention (anti GM-CSF antibodies), which antibodies have GM-CSF antagonistic activity. GM-CSF antagonistic activity is defined as the ability to block the interaction of GM-CSF with its receptor on GM-CSF receptor-containing cells and/or reduce stimulation of cell proliferation of GM-CSF reactive cells in the presence of GM-CSF below the normal level of GM-CSF stimulation of cell proliferation of such cells. These antibodies bind to GM-CSF and thereby prevent the binding of GM-CSF to its cellular receptors. Preferably such antibodies are monoclonal antibodies.

The invention further provides antibodies which specifically bind to the antibodies against the polypeptides of the invention (anti-anti GM-CSF, or anti-idiotypic antibodies). These anti-idiotypic antibodies mimic GM-CSF, thereby competing with GM-CSF for binding to its cellular receptors and blocking the GM-CSF receptor sites on GM-CSF receptor-containing cells, reducing stimulation of cell proliferation of GM-CSF reactive cells in the presence of GM-CSF below the normal level of GM-CSF stimulation of cell proliferation of such cells. Preferably, the anti-idiotypic antibodies are monoclonal antibodies.

The antibodies of the invention are useful for treating various diseases which are attributed to the actions of GM-CSF. They are also useful in studies of the mechanism of binding of GM-CSF to its cellular receptors and/or in receptor-based screening systems to identify other antagonists and/or agonists of GM-CSF.

BRIEF DESCRIPTION OF THE FIGURES

FIG. 1. Recognition of GM-CSF and peptide 110-127 by antibody 349-6. Elisa assay conditions are described in Example C. Rabbit anti-serum 349-6 was diluted 1:500 prior to coating wells with 50 µl. Rabbit pre-immune serum did not bind GM-CSF or peptide 110-127.

FIG. 3. Recognition of rabbit antibody 345-6 by sheep antibody 1418 by Elisa analysis. Microtiter plate wells were coated with 0.52 µg of rabbit antiserum 345-6 as antigen. Following washing and blocking procedures as described in Example C, wells were coated with varying dilutions of sheep anti-serum 1418. Binding was detected with donkey anti-sheep IgG conjugated with horseradish peroxidase.

FIG. 5. Displacement of $^{125}$I-GM-CSF from receptors by antibody 345-6. (A) 4×10$^6$ KG-1 cells were incubated with 0.20 nM $^{125}$I-GM-CSF (85,760 cpm) and various concentrations of antibody for 1 hour at 22° C. Specific binding of $^{125}$I-GM-CSF in the absence of antibody was 3072 cpm. (B) Placental membranes were incubated with 0.49 nM $^{125}$I-GM-CSF (7.2×10$^5$ cpm) and antibody for 1 hour at 22° C. 4110 cpm was specifically bound in the absence of antibody.

FIG. 6. Competitive displacement of $^{125}$I-GM-CSF from receptors by sheep antibody 1418. (A) 5×10$^6$ KG-1 cells were incubated with 0.54 nM $^{125}$I-GM-CSF (2.02×10$^5$ cpm) in the absence and presence of antibody for 1½ hours at 4° C. Specific binding observed in control assays lacking antibody was 3515 cpm. (B) 4.85 nM $^{125}$I-GM-CSF (68,850 cpm) was incubated with placental membranes for 1 hour at 22° C. in the presence of various dilutions of antibody. Specific binding observed in the absence of antibody was 16,397 cpm.

DESCRIPTION OF THE INVENTION

All references cited herein are hereby incorporated in their entirety by reference.

As explained above, the polypeptides of the invention can contain as many as about 23 amino acid residues (Formulas I and II). The antibodies of the invention prepared against these polypeptides are directed against one or more antigenic determinants (epitopes) within the polypeptides. It is well known in the art that antigenic determinants generally contain at least about 5 amino acid residues [Ohno et al., Proc. Natl. Acad. Sci. USA 82:2945 (1985)].

Therefore, the polypeptides of the invention can contain from about 5 to about 23 amino acid residues, and they can have amino acid sequences corresponding to part or all of the above-mentioned sequences (Formulas I and II). Whether a given polypeptide falls within the scope of this invention can readily be determined by routine experimentation using the methods described below.

Peptide Synthesis

Peptides of the invention are synthesized by standard techniques, e.g. Stewart and Young, *Solid Phase Peptide Synthesis*, 2nd Ed. (Pierce Chemical Company, Rockford, Ill. 1984). Preferably a commercial automated synthesizer is used, e.g. Vega Biochemicals (Tuscon, Ariz.) models 296A or B, or Applied Biosystems, Inc. (Foster City, Calif.) model 430A.

The protected peptide of Formula II can be assembled by solid phase synthesis on a cross-lined polystyrene support starting from the carboxyl terminal residue and adding amino acids in a step-wise fashion until the entire 23-residue chain has been formed. The synthesis can be performed on a fully automated peptide synthesizer (Applied Biosystems, Inc. model 430A). The following references are guides to the chemistry employed during synthesis: Merrifield, J. Amer. Chem. Soc., 85: 2149 (1963); Kent et al., pg. 185, in Peptides 1984, Ragnarsson, Ed. (Almquist and Weksell, Stockholm 1984); Kent et al., pg. 217 in Peptide Chemistry 84, Izumiya, Ed. (Protein Research Foundation, B. H. Osaka 1985); Merrifield. Science, 232: 341–347 (1986) and references cited in this last reference.

In solid state synthesis it is most important to eliminate synthesis by-products, which are primarily termination, deletion, or modification peptides. Most side reactions can be eliminated or minimized by use of clean, well characterized resins, clean amino acid derivatives, clean solvents, and the selection of proper coupling and cleavage methods and reaction conditions, e.g. Barany and Merrifield, The Peptides, Cross and Meienhofer, Eds., Vol. 2, pgs. 1–284 (Academic Press, New York 1979). It is important to monitor coupling reactions to determine that they proceed to completion so that deletion peptides missing one or more residues will be avoided. The quantitative ninhydrin reaction is useful for that purpose, Sarin et al. Anal. Biochem, 117:147 (1981). Nα-t-butyloxycarbonyl (t-Boc)-amino acids can be used with appropriate side chain protecting groups stable to the conditions of chain assembly but labile to strong acids. After assembly of the protected peptide chain, the protecting groups can be removed and the peptide anchoring bond can be cleaved by the use of low then high concentrations of anhydrous hydrogen fluoride in the presence of a thioester scavenger, Tam et al., J. Amer. Chem. Soc., 105:6442 (1983).

Other organic synthetic methodology to be employed includes solution-phase synthesis as is described in *The Peptides: Analysis, Synthesis and Biology*, Vol. I Major Methods of Peptide Bond Formation, E. Gross and J. Meienhofer editors, Academic Press (1979) and *Chemistry of the Amino Acids*, Greenstein and Winite editors, John Wiley and Sons (1961).

Additionally, the peptides can be made using well known recombinant DNA molecules. Complementary DNAs (cDNAs) that code for the positive strand messenger RNA (mRNA) coding for the desired polypeptides can be isolated or synthesized and inserted into appropriate vectors and host cells. The exact sequence of bases in the cDNA will be determined by the sequence of amino acids of the desired polypeptide as well as the expression host utilized. Certain hosts, e.g., bacteria and yeast, have preferred codons that are utilized to translate certain amino acids, See Bennetzen and Hall, J. Biol. Chem., 257: 3026–3031 (1982) and Boer and Kastelian, "Biased Codon Usage;: An Exploration of its Role in Optimization of Translation", chapter 8, pp. 225–283, Benzikoff and Gold, Eds., *Biotechnology Series,* 1985. These recombinantly produced polypeptides can then be isolated by methods known to those skilled in the art. In the present invention, affinity chromatography would be a useful and preferred method of isolation because the polypeptides are designed to specifically react with GM-CSF receptors; and/or GM-CSF-reactive antibodies.

The polypeptides of the present invention can also be obtained by chemical cleavage or proteolytic digestion of longer polypeptides followed by isolation and purification of the desired cleavage products.

Antibody Production

The following methods can be employed to product polyclonal antibodies that are GM-CSF antagonists. An appropriate amount of antigen (e.g., peptide 110-127, or other carboxyl terminal region) can be injected into a suitable animal to raise antibodies. The preferred animals are rabbits for raising antibodies to the carboxyl terminal peptides and sheep for raising antibodies to the antibodies. The amount of antigen injected will depend on the size, weight and health of the animal, and injection can be by any route, with subcutaneous or intradermal injection being preferred. Multiple injections may increase the immune response and such injections may occur as frequently as weekly or as infrequently as every several months. The injected solution is preferably buffered with an appropriate biological buffer such as TrisHCl (pH 6.8). The solution can also contain general immune stimulators such as pertussis vaccine, adjuvant (e.g., Freund's complete adjuvant) or both, and a stabilizing agent such as 1/10,000 thimersol. The whole serum of the sensitized animals containing the GM-CSF antagonistic antibodies can be used to block GM-CSF activity, but preferably the antibodies are purified by techniques known to those skilled in the art. A particularly useful and preferred technique is affinity chromatography. Such chromatography would utilize GM-CSF, GM-CSF receptors or preferably the carboxyl terminal region used for sensitization, as the affinity ligand attached to any one of a number of commercially available chromatography resins.

When the source of the antibodies is rabbits, purification can preferably take place by sequentially dialyzing against a suitable buffer (e.g., 0.1M sodium acetate pH 5.5 overnight at 4° C.), centrifugation to remove insoluble material, adsorption onto ion exchange chromatography (such as S-Sepharose, Pharmacia, equilibrated with the 0.1M sodium acetate above), elution with salt (e.g., 1.0M NaCl in 0.05M sodium acetate pH 5.5), adsorption onto a Protein A-Sepharose column (commercially available from Pharmacia [e.g., 17-0628-01, 17-0629-01], Sigma Chemical Co. [e.g. P7786, P3391, P6649] and Miles-Yeda Ltd. [e.g., 79-700]) equilibrated with a basic buffer (about 1.5M glycine, pH 8.8) and elution with an acid buffer (0.1M citric pH 2.5). The use of Protein A in purification of membrane proteins using a high efficiency immunomatrix is described in Schneider et al., J. Biol. Chem., 257: 10766–10769 (1982).

The production of monoclonal antibodies that specifically bind to the carboxyl region of GM-CSF or antibodies against such anti-carboxyl antibodies can be produced by techniques that are well known to those skilled in the art. Such monoclonal antibodies are generally the result of a three stage produced: sensitization, fusion and screening.

Sensitization (immunization) of the host animal, preferably mouse, rat, rabbit or sheep can be several injections of the antigen (either the carboxyl region or the anticarboxyl antibody). The antigen can be applied in any suitable form, e.g., in complete Freund's Adjuvant (CFA) emulsified with phosphate buffered saline (PBS, preferably in a ratio of 1:1). The number of injections and the quantity of antigen administered must be such that useful quantities of suitably primed splenocytes are produced to be used in the fusion. Preferably, immunization consists of three intraperitoneal injections with 10 μg of antigen at about 2 week intervals, followed by a further boost of 10 μg of antigen in phosphate buffered saline administered intravenously and 10 μg of antigen in CFA/PBS intraperitoneally. Spleens of the immunized animals are removed and spleen suspensions can be prepared by well-known techniques.

The spleen cell from immunized animals can be fused to a self-propagating cell line, e.g., a mouse myeloma cell, as described in Kohler & Milstein, Nature, 256: 495–497 (1975). Fused cells are chosen over unfused cells by culturing the mixture in a medium that will eliminate the unfused cell line, e.g., in a HAT medium (a culture medium comprising hypoxanthine, aminopterin and thymidine). The unfused spleen cells that are non-self-propagating (e.g. non-malignant) will normally stop growing after a short period of time, whereas the fused cells that carry a selection gene from the splenocytes, e.g. HGPRT$^+$ (hypoxanthine guanosyl phosphoribosyl transferase), can grow in the HAT medium.

Once antibodies have been produced to a carboxyl-terminal region, they can be assayed for GM-CSF antagonistic activity and purified as described below.

Screening

1. Cell Proliferation Assay

The assay for GM-CSF is based on stimulation of proliferation of suitable cells such as KG-1 cells, a cell line established from the bone marrow of a patient with acute myelogenous leukemia. AML-193 cells can also be used in this assay. AML-193 are cells as described in B. Lange et al., Blood, 70: 192–199 (1987). Cells are incubated in microtiter plate wells with dilutions of GM-CSF for about 6 days and then incubated for about an additional 4 hours with the tetrazolium salt MTT (3-(4,5-dimethylthiozol-2-yl)-2,5-diphenyltetrazolium bromide). MTT is converted by mitochondrial dehydrogenase enzymes to a colored reaction product, formazan (Mosmann, I. (1983) J. Immunological Methods 65, 55–63). The formazan is extracted with acidified isopropanol and measured spectrophotometrically. The observed optical density is directly proportional to the $\log_2$ cell concentration. The results are expressed as $\Delta$O.D., where $\Delta$O.D. is the optical density of the sample minus the optical density of a baseline control lacking GM-CSF.

2. GM-CSF Receptor Binding Assay

GM-CSF is radioiodinated by the method of Bolton and Hunter (Bolton, A. E. & Hunter, W. M. (1973) Biochem. J. 133, 529–539) and purified by gel filtration on a Sephadex G-25 column (PD-10, Pharmacia). The resulting $^{125}$I-GM-CSF has a specific radioactivity of about 1–3×10$^6$ μCi/μMole and a stoichiometry of 0.4–1.2 moles $^{125}$I per mole of GM-CSF. The specific radioactivity and stoichiometry can be determined by the self displacement method (Calvo et al., (1983) Biochem. J. 212:259–264). $^{125}$I-GM-CSF has the same biological activity as unlabeled GM-CSF, measured by the KG-1 cell proliferation assay.

Assays to measure $^{125}$I-GM-CSF binding to receptors on KG-1 cells (high affinity site $K_d$=6.7 pM, 70 sites/cell; low affinity site $K_d$=0.73 nM, 2700 sites/cell) or AML-193 cells contain about: 0.2–0.5 nM $^{125}$I-GM-CSF, 4–6×10$^6$ KG-1 cells, and Iscove's Modified Dulbecco's Medium containing 10% fetal calf serum (IMDM-10% FCS), in a total volume of 0.4 ml. The samples are incubated at about 22° C. or 4° C. for 1 hour or 2 hours, respectively. Centrifugation for 2½ minutes at 600×g yields a cell pellet which is washed twice with IMDM-10% FCS.

Placental membranes are prepared by homogenization, centrifugation to remove the 100×g fraction, and thorough washing of the 27,300×g fraction. Protease inhibitors may be present in the homogenization and wash buffers. To quantitate binding of $^{125}$I-GM-CSF to receptors on placental membranes ($K_d$=0.86 nM), placental membranes are incubated for 1 hour with 0.5–5.0 nM $^{125}$I-GM-CSF and IMDM-10% FCS in a total volume of 0.4 ml. Following incubation for about 1 hour at about 22° C., samples are centrifuged for about 2½ minutes at 800×g and the placental membrane pellet washed twice with IMDM-10% FCS. Cell pellets are counted on a gamma counter. Saturating concentrations of unlabeled GM-CSF are added to control assays to measure non-specific binding.

To measure the displacement of $^{125}$I-GM-CSF from receptors by polyclonal antibodies, antisera or pre-immune sera are included in the binding assays. Antibodies that recognize GM-CSF are incubated for about 10 minutes with $^{125}$I-GM-CSF prior to initiating binding by the addition of KG-1 cells, AML-193 cells or placental membranes. The sheep polyclonal antibody 1418, which recognized the GM-CSF receptor, is pre-incubated for about 10 minutes with KG-1 cells, AML-193 cells or placental membranes. Binding is initiated by $^{125}$I-GM-CSF addition.

Although the antagonistic effects of the antibodies of the invention are illustrated herein using AML-193 cells, KG-1 cells or placental membranes, it must be understood that the antibodies will also be effective on the numerous other types of cells and tissues which bear GM-CSF receptors on their surfaces.

3. Enzyme-Linked Immunosorbent Assay (ELISA)

Rabbit and sheep sera are screened for specific binding of antigens by employing a direct solid-phase ELISA at room temperature. A 96-well microtiter plate (Becton-Dickinson) is coated with about 50 μl of antigen per well for about 1 hour at room temperature. The plate is washed about 5 times with Tris-buffered saline (TBS) containing 0.1% Tween 20. The plate is subsequently blocked with 1% bovine serum albumin for about 1 hour, and again washed 5 times with TBS. Blocking with immunoglobulin is omitted from the procedure for Antibody 1418. The wells are coated with the antibody to be tested for about 1 hour, washed 5 times with TBS, and coated with 2.5 ng of goat anti-rabbit IgG conjugated with horseradish peroxidase (or 5.0 ng donkey anti-sheep IgG). Following incubation for 1 hour, the plate is washed 5 times with TBS. The plate is developed by adding 2,2'-azino-bis[3-ethyl-benzthiazoline sulfonate] and hydrogen peroxide to each well. The horseradish peroxidase reaction product can be detected colorimetrically 20 minutes after the addition of enzyme substrates. Control wells are also developed in which one of the assay components is missing (antigen, antibody, peroxidase-labeled antibody).

4. Fluorescence-Activated Cell Sorter Analysis of Anti-idiotypic Antibody 1418.

Assays to measure direct bending of anti-idiotypic antibody to receptors on KG-1 cells are performed as follows: 4×10$^6$ cells (KG-1) are washed with Iscove's Modified Dulbecco's Medium containing 10% fetal calf serum (IMDM-10% FCS) and centrifuged at 1,000 RPM for 5 min. at 4° C. to obtain a pellet. The supernatant is removed and cells are incubated with 100 μl of GM-CSF (10 ng/100 μl in IMDM-10% FCS) or 100 μl of IMDM-10% FCS for 10 min. at 4° C. The cells are washed with 1 ml of IMDM-10% FCS, centrifuged, the supernatant removed, and cells are incubated with 100 μl of antibody or antiidiotypic antibody for 30 minutes. The cells are washed twice with 2–3 ml of IMDM-10% FCS and centrifuged, the supernatant is removed and the cells are incubated with 100 μl of goat anti-rabbit or anti-sheep IgG (as appropriate) conjugated with fluorescein (FITC; 1.5 mg/ml in IMDM-10% FCS) for 30 minutes. The cells are then washed twice with IMDM-10% FCS, and the resulting pellet of cells is resuspended in 1 ml of phosphate buffered saline at pH 7.2. The cells are then analyzed in an instrument such as a Becton-Dickenson Model 440 analyzer. Negative controls are handled in a similar manner except that the antibody or anti-idiotypic antibody is omitted.

5. Direct Binding Analysis of Anti-Idiotypic Antibody by Immunofluorescence.

JAR cells available from ATCC No. HTB 144, (at 5×10$^4$ cells per well) are seeded into two-well chamber slides. After 3 days of incubation, medium is removed, and the cells are washed 3 times with cold TBS. The buffer is removed and 0.5 ml of anti-idiotypic antibody is added and incubated at 4° C. for 30 minutes. The cells are washed with 1.0 ml of PBS, the buffer is removed and goat anti-sheep IgG conjugated with fluorescein (FITC) is added and incubated at 4° C. for 30 minutes. The cells are washed again 3 times and mounted in 20% glycerol in TBS. Cells are examined with a LEITZ fluorescent microscope.

According to this invention, mammals are administered an antibody or anti-idiotypic antibody (or peptide) in an amount sufficient to inhibit aberrant cell growth under paracrine or autocrine control by GM-CSF. The amount, frequency and period of administration can vary depending upon age of patient, severity of GM-CSF response and response to antibody therapy. Administration can be subcutaneous, intradermal, parenteral, intravenous. The antibody (or peptide) can be administered in any number of conventional dosage forms including in 0.9% saline/5% human serum albumin, or with any of the other well known physiologically acceptable carriers. Antibody (or peptide) can be administered at 10 to 100 mg/m$^2$ every other day for eight to ten treatments. Continuous infusion treatments can be performed at 30–80 mg/m$^2$ per day for eight days for total dosage of 250–1000 mg.

A GM-CSF antagonist could be used in conjunction with a therapeutic agent directed at proliferating cell populations. The antagonist would block blast-cell proliferation, thus providing protection from the primary chemotherapy. Following chemotherapy/GM-CSF antagonist treatment, GM-CSF could be administered to help stimulate development of the protected blast-cell population. Administration of the GM-CSF antagonists for this use would be the same as above.

EXAMPLES

A. Peptide Synthesis

Peptides were synthesized using the solid-phase method described by Merrifield [R. B. Merrifield, J. Am. Chem. Soc., 85, 2149–2154 (1963)]. The t-butyloxycarbonyl amino protecting group, symmetrical anhydrides, and the Applied Biosystems Model 430A solid-phase peptide synthesizer were employed. Following removal of protecting groups, the peptides were cleaved from the resin with hydrogen fluoride. Crude peptides recovered after cleavage from the resin were analyzed by reverse-phase HPLC on a Rainin Dynamax C-8 column (12μ particle size 300 A pore size, 4.6 mm×250 mm).

B. Production of Antisera

Rabbit Immunization 2 mg of antigen (peptide 110-127 or human GM-CSF) was dissolved in 0.4 ml 0.5M Tris HCl (pH 6.8) and 0.1 ml pertussis vaccine (strain 18334, heat killed). 0.5 ml Freund's complete adjuvant was added and the sample homogenized in a syringe. Rabbits were immunized with 1 ml of the sample by 0.1 ml (200 μg antigen) intradermal injections.

Purification of Rabbit Antipeptide 110-127 IgG from Rabbit Serum 345-6

Dot blot analysis for rabbit IgG was achieved by spotting an aliquot of the sample to be tested on nitrocellulose, blocking with BSA (bovine serum albumin), incubating with alkaline phosphatase-labeled anti-rabbit IgG, and staining with reagents to detect alkaline phosphatase by a colorimetric reaction.

Rabbit serum 345-6 (45 ml, 26 mg/ml protein) was dialyzed against 0.1M sodium acetate (pH 5.5) overnight at 4° C. Following centrifugation at 10,000 rpm for 30 minutes to remove any insoluble material, the sample was applied to an S-Sepharose column equilibrated with the same buffer. The eluant obtained with 0.05M sodium acetate (pH 5.5), 1.0M NaCl contained 82 mg total protein which was positive by dot blot analysis for rabbit IgG. This sample was adsorbed to a Protein A-Sepharose column equilibrated with 1.5M glycine (pH 8.8). The protein fraction (78 mg) which was not adsorbed by the column was negative by dot blot analysis. Elution with 0.1M glycine (pH 2.5) yielded 23 mg protein (Lowry assay using IgG as a standard) which stained positive for rabbit IgG on a nitrocellulose dot blot. The sample was judged to be approximately 98% pure IgG by the degree of Coomassie Blue staining following sodium dodecylsulfate polyacrylamide gel electrophoresis (SDS-PAGE).

Sheep Immunization

Sheep antiserum 1418 was produced by immunization with the rabbit IgG purified from anti-serum 345-6. 1.5 mg of 345-6 IgG in 0.5 ml phosphate buffered saline was added to 0.5 ml Freund's complete adjuvant and mixed thoroughly to form an emulsion. The 349-6 antibody was purified according to the method of Schneider et al., J. Biol Chem., 257(18): 10766–10769 (1982). Samples were injected subcutaneously. Boosts were performed in an identical manner except that incomplete Freund's adjuvant was employed.

The immunization schedules for rabbits and sheep are given in the Table III.

TABLE III

| Immunization Schedule | | | |
|---|---|---|---|
| Animal | Designation | Antigen | Day of Immunization |
| rabbit | 349-6 | GM-CSF | 0, 185 |
| rabbit | 345-6 | peptide 110-127 | 0, 113, 298 |
| sheep | 1418 | 345-6 IgG | 0, 23, 47, 74, 94 |

C. Enzyme-linked Immunosorbent Assay (ELISA)

Rabbit and sheep sera were screened for specific binding of antigens by employing a direct solid-phase ELISA at room temperature. A 96-well microtiter plate (Becton-Dickinson) was coated with 50 μl of antigens per well for 1 hour at room temperature. The plate was washed 5 times with Tris-buffered saline (TBS) containing 0.1% Tween 20. The plate was subsequently blocked with 1% bovine serum albumin for 1 hour, washed 5 times with TBS, blocked with 0.1% immunoglobulin for 1 hour, and again washed 5 times with TBS. Blocking with immunoglobulin was omitted from the procedure for Antibody 1418. The wells were coated with the antibody to be tested for 1 hour, washed 5 times with TBS, and coated with 2.5 ng of goat anti-rabbit IgG conjugated with horseradish peroxidase (or 5.0 ng of donkey anti-sheep IgG conjugated with horseradish peroxidase). Following incubation for 1 hour, the plate was washed 5 times with TBS.

The plate was developed by adding 2,2'-azino-bis[3-ethylbenzthiazoline sulfonate] and hydrogen peroxide to each well. The horseradish peroxidase reaction product was detected spectrophotometrically at 414 nm 20 minutes after the addition of enzyme substrates. Control wells were also developed in which one of the assay components was missing (antigen, antibody or peroxidase-labeled antibody).

Figure 1:
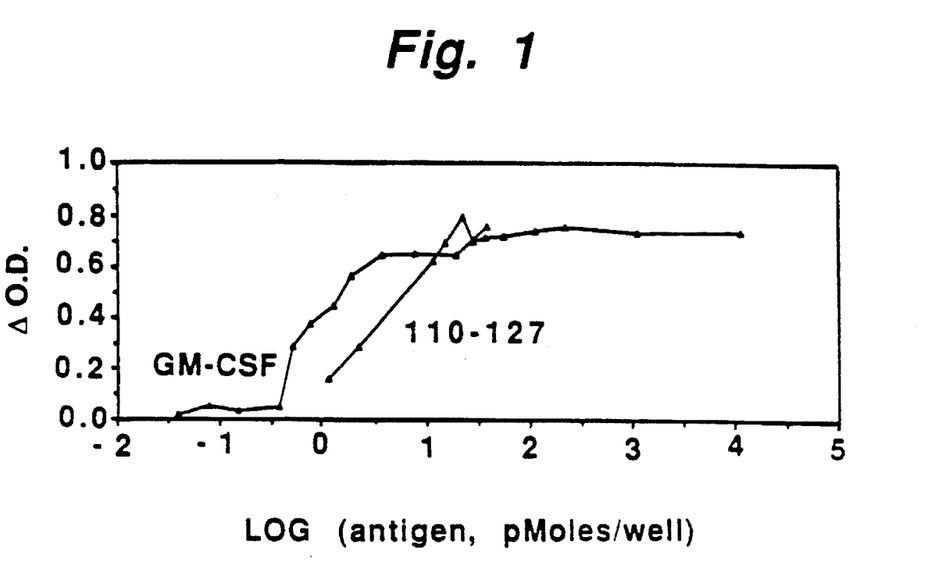
Figure 2:
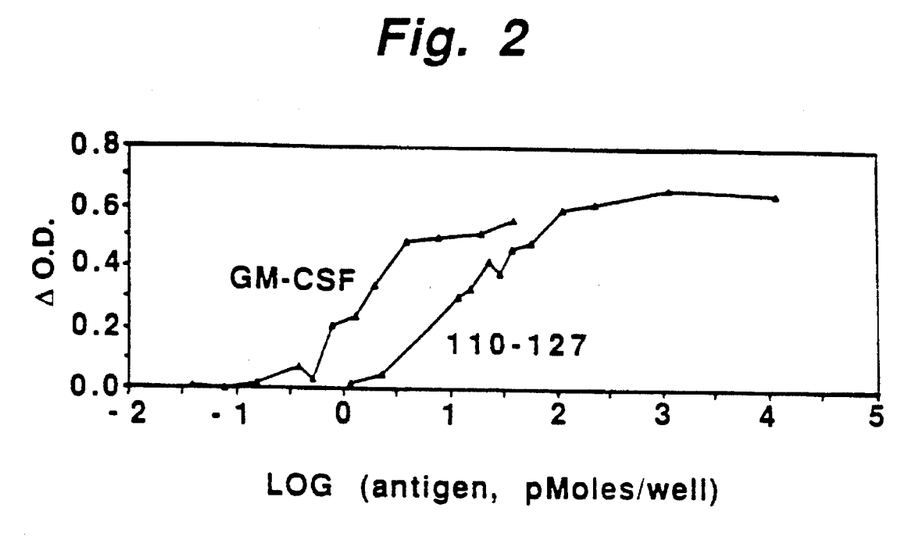
FIG. 2. The binding of GM-CSF and peptide 110-127 by antibody 345-6 in immunosorbent assays. Rabbit anti-serum 345-6 was diluted 1:500 prior to coating wells with 50 µl.
Figure 3:
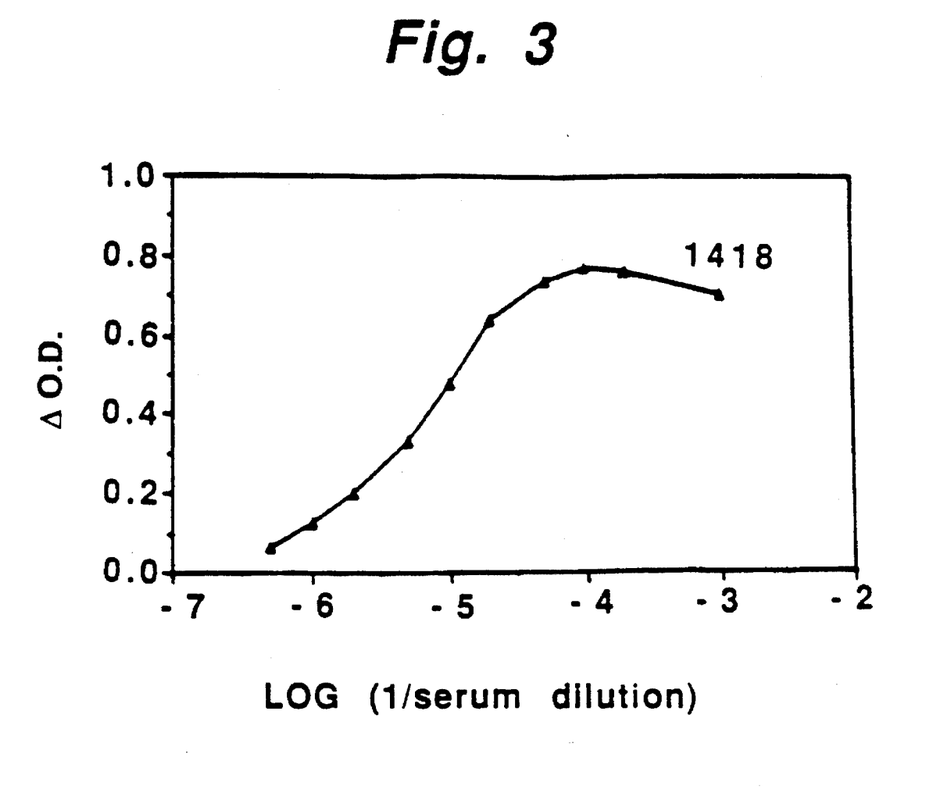

FIGS. 1, 2 and 3 demonstrate the binding of GM-CSF and fragment 110-127 by anti GM-CSF (antibody 349-6, FIG. 1) and anti 110-127 (antibody 345-6, FIG. 2) as shown by ELISA. FIG. 3 shows the binding of antibody 345-6 by antibody 1418 (the anti-idiotypic antibody to antibody 345-6).

D. GM-CSF Receptor Binding Assay

GM-CSF (an article of commerce available, e.g., from Genzyme Corporation, Boston, Mass.) was radioiodinated by the method of Bolton and Hunter [Bolton, A. E. & Hunter, W. M., Biochem., J., 133: 529–539 (1973)] and purified by gel filtration on a Sephadex G-25 column (PD-10, Pharmacia). The resulting $^{125}$I-GM-CSF had a specific radioactivity of $1-3\times10^6$ μCi/μMole and a stoichiometry of $0.4–1.2$ moles $^{125}$I per mole GM-CSF. The specific radioactivity and stoichiometry were determined by the self-displacement method [Calvo, J. C., Radicella, J. P., & Charreau, E. H., Biochem. J., 212: 259–264 (1983)]. $^{125}$I-GM-CSF had the same biological activity as unlabeled GM-CSF, measured by the KG-1 cell proliferation assay. Assays to measure $^{125}$I-GM-CSF binding to receptors on KG-1cells (high affinity site $K_d$=6.7 pM, 70 sites/cell; low affinity site $K_d$=0.73 nM, 2700 sites/cell) contained: 0.2–0.5 nM $^{125}$I-GM-CSF, $4-6\times10^6$ KG-1 cells, and Iscove's Modified Dulbecco's Medium containing 10% fetal calf serum (IMDM-10% FCS), in a total volume of 0.4 ml. The samples were incubated at 22° C. or 4° C. for 1 hour or 2 hours, respectively. Centrifugation for 2½ minutes at 600×g yielded a cell pellet which was washed twice with IMDM-10% FCS.

Placental membranes were prepared by homogenization, centrifugation to remove the 100×g fraction, and thorough washing of the 27,300×g fraction. Protease inhibitors were present in the homogenization and wash buffers. To quantitate binding of $^{125}$I-GM-CSF to receptors on placental membranes ($K_d$=0.86 nM), placental membranes were incubated for 1 hour with 0.5–5.0 nM $^{125}$I-GM-CSF and IMDM-10% FCS in a total volume of 0.4 ml. Following incubation for 1 hour at 22° C., samples were centrifuged for 2½ minutes at 800×g and the placental membrane pellet washed twice with IMDM-10% FCS. Cell pellets were counted on a gamma counter. Saturating concentrations of unlabeled GM-CSF were added to control assays to measure nonspecific binding.

To measure the displacement of $^{125}$I-GM-CSF from receptors by polyclonal antibodies, antiserum or pre-immune serum was included in the binding assays. Antibodies which recognize GM-CSF were pre-incubated for 10 minutes with $^{125}$I-GM-CSF prior to initiating binding by the addition of KG-1 cells or placental membranes. The sheep polyclonal antibody 1418, which recognizes the GM-CSF receptor, was pre-incubated for 10 minutes with KG-1 cells or placental membranes. Binding was initiated by $^{125}$I-GM-CSF addition.

Figure 4:
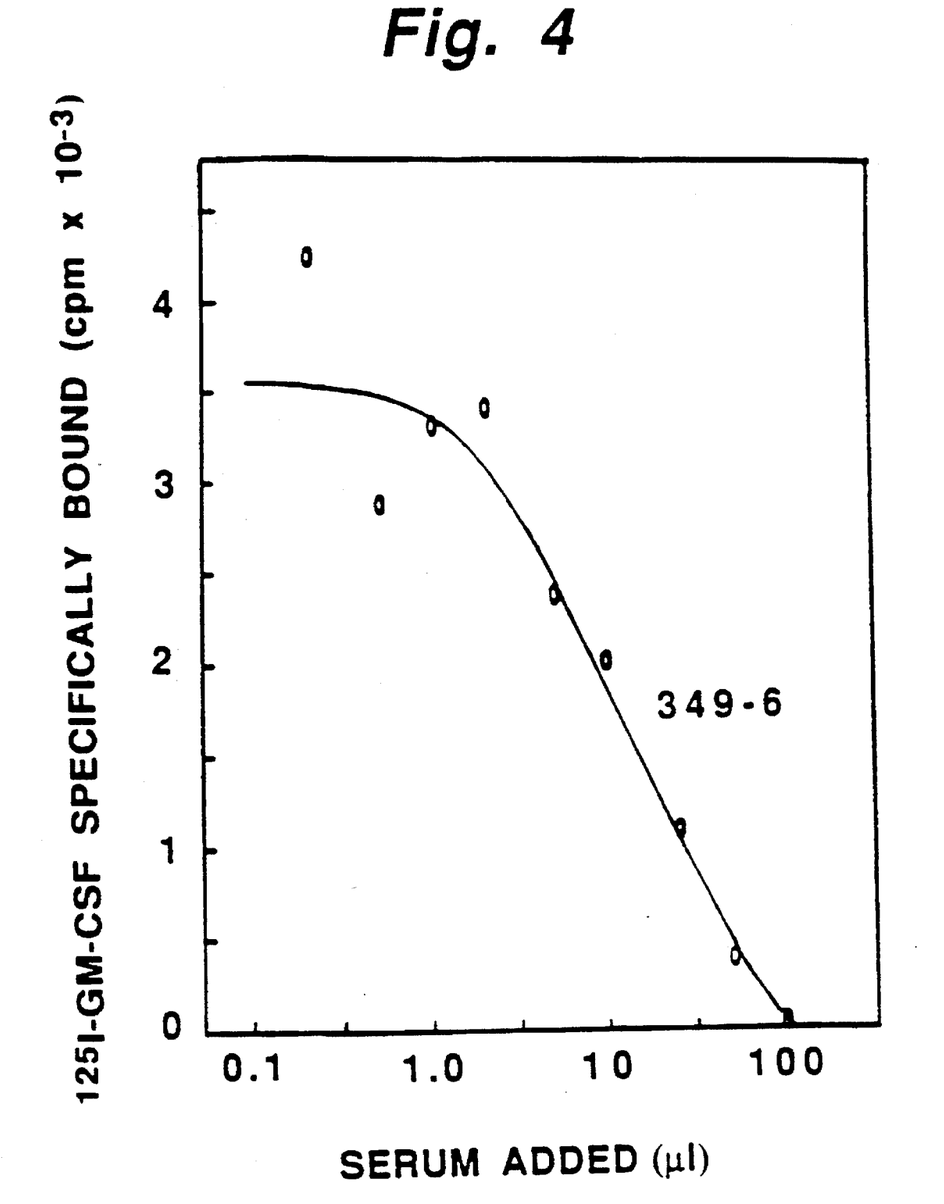
FIG. 4. Displacement of $^{125}$I-GM-CSF from placental membrane receptors by antibody 349-6. Placental membranes were incubated with 0.49 nM $^{125}$I-GM-CSF (40,600 cpm) in the presence and absence of antibody for 1 hour at 22° C. $^{125}$I-GM-CSF specifically bound in the absence of antibody was 3456 cpm.
Figure 5:
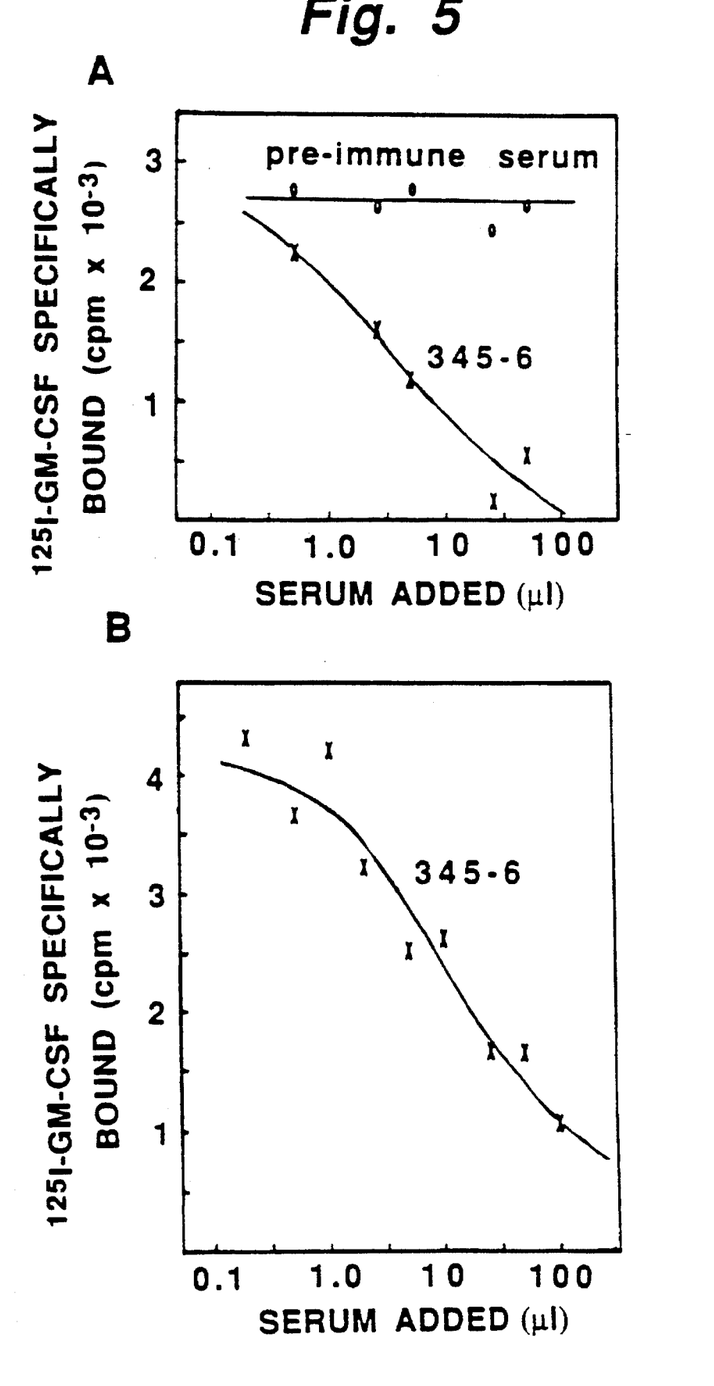
Figure 6:
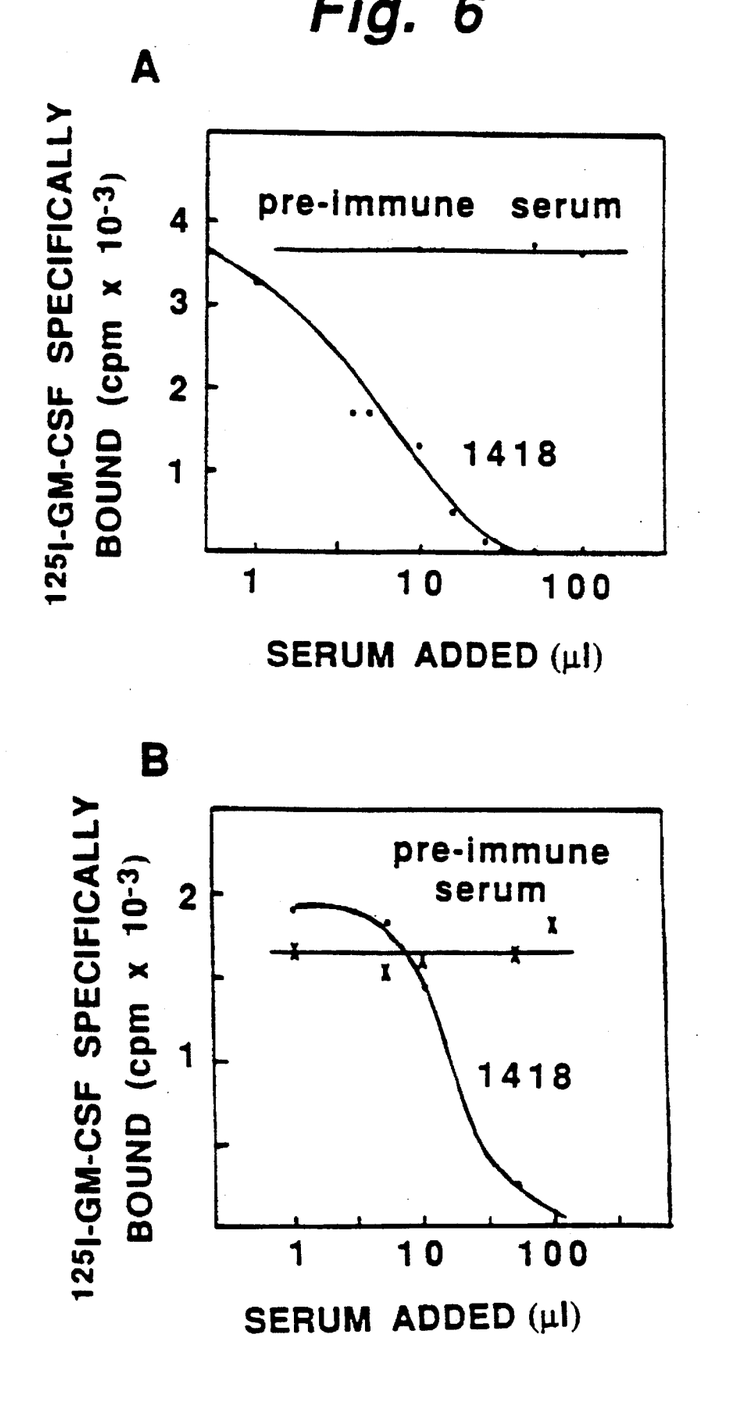

FIGS. 4, 5, and 6 demonstrate the competitive displacement of $^{125}$I-GM-CSF from receptors by antibodies 349-6 (FIG. 4), 345-6 (FIG. 5) and 1418 (FIG. 6) in the GM-CSF Receptor Binding Assay.

E. KG-1 Cell Proliferation Assay

The assay for GM-CSF is based on stimulation of proliferation of KG-1 cells, a cell line established from the bone marrow of a patient with acute myelogenous leukemia. Cells are incubated in microtiter plate wells with dilutions of GM-CSF for 6 days and then incubated for an additional 4 hours with the tetrazolium salt MTT (3-(4,5-dimethylthiozol-2-yl-)-2,5-diphenyltetrazolium bromide). MTT is converted by mitochondrial dehydrogenase enzymes to a colored reaction product, formazan [Mosmann, T., J. Immunological Methods 65: 55–63 (1983)]. The formazan is extracted with acidified isopropanol and measured spectrophotometrically. The observed optical density ($\lambda$=570 nm) is directly proportional to the $\log_2$ cell concentration. The results are expressed as $\Delta$O.D., where $\Delta$O.D. is the optical density of the sample minus the optical density of a baseline control lacking GM-CSF.

The following table demonstrates the effect of sheep anti-idiotypic antibodies (antibodies to antibodies to the 110-127 fragment) on GM-CSF stimulation of KG-1 cell proliferation. Values in the table are the optical density of the sample minus the optical density of a baseline control lacking GM-CSF ($\Delta$O.D.). Microtiter plate wells contained 10 ng/ml GM-CSF, $10^4$ KG-1 cells, and sheep anti-idiotypic antibody serum or pre-immune serum in a total volume of 100 μl. Control wells which did not contain serum had $\Delta$O.D values of 0.087 and 0.019 for Experiments I and II respectively.

TABLE IV

Effect Of Sheep Anti-idiotypic Antibody (1418) On GM-CSF Stimulation Of KG-1 Cell Proliferation

| Serum Dilution | Experiment I | | Experiment II | |
|---|---|---|---|---|
| | Pre-immune | 1418 | Pre-immune | 1418 |
| 1:10 | 0.106 | 0.059 | 0.048 | 0.002 |
| 1:20 | 0.100 | 0.048 | 0.053 | −0.016 |
| 1:40 | 0.031 | 0.012 | 0.049 | −0.003 |
| 1:80 | 0.030 | −0.005 | 0.056 | −0.006 |
| 1:160 | 0.043 | −0.029 | 0.030 | 0.002 |
| 1:320 | 0.029 | 0.001 | 0.032 | 0.036 |

F. Protein Determinations

Protein concentrations were determined by the method of Lowry [Lowry et al., J. Biol. Chem. 193:265 (1951)] using bovine serum albumin as a standard unless otherwise noted.

Many modifications and variations of this invention may be made without departing from its spirit and scope, as will become apparent to those skilled in the art. The specific embodiments described herein are offered by way of example only, and the invention is to be limited only by the terms of the appended claims.

We claim:

1. A polypeptide having an amino acid sequence:

H—Ser—Phe—Lys—Glu—Asn—Leu—Lys—

Asp—Phe—Leu—Leu—Val—Ile—Pro—

Phe—Asp—Cys—Trp—Glu—Pro—Val—

Gln—Glu—OH, or a subsequence thereof wherein the polypeptide has from about 18 to about 23 amino acid residues such that antibodies having GM-CSF antagonistic activity can be raised against said polypeptide.

2. A polypeptide which has an amino acid sequence selected from the group consisting of H—Ser—Phe—Lys—Glu—Asn—
Leu—Lys—Asp—Phe—Leu—
Leu—Val—Ile—Pro—Phe—
Asp—Cys—Trp—Glu—Pro—
Val—Gln—Glu—OH and H—Leu—Lys—Asp—Phe—Leu—
Leu—Val—Ile—Pro—Phe—
Asp—Cys—Trp—Glu—Pro—
Val—Gln—Glu—OH.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
      ( A ) LENGTH: 23 amino acid residues
      ( B ) TYPE: amino acid
      ( D ) TOPOLOGY: linear    ( i i ) MOLECULE TYPE: peptide    ( x i ) SEQUENCE DESCRIPTION: SEQ ID NO: 1:

Xaa Xaa Xaa Xaa Xaa Xaa Xaa Xaa Xaa Xaa Xaa Xaa Xaa Xaa Xaa
             5                       10                     15

Xaa Cys Trp Xaa Xaa Xaa Xaa Xaa
             20

( 2 ) INFORMATION FOR SEQ ID NO: 2:

( i ) SEQUENCE CHARACTERISTICS:
      ( A ) LENGTH: 23 amino acid residues
      ( B ) TYPE: amino acid
      ( D ) TOPOLOGY: linear ( x i ) SEQUENCE DESCRIPTION: SEQ ID NO: 2:

Ser Phe Lys Glu Asn Leu Lys Asp Phe Leu Leu Val Ile Pro Phe
                 5                   10                      15

Asp Cys Trp Glu Pro Val Gln Glu
             20

( 2 ) INFORMATION FOR SEQ ID NO: 3:

( i ) SEQUENCE CHARACTERISTICS:
        ( A ) LENGTH: 18 amino acid residues
        ( B ) TYPE: amino acid
        ( D ) TOPOLOGY: linear     ( x i ) SEQUENCE DESCRIPTION: SEQ ID NO: 3:

Leu Lys Asp Phe Leu Leu Val Ile Pro Phe Asp Cys Trp Glu Pro
                 5                   10                      15

Val Gln Glu